(12) United States Patent
Yoshikawa et al.

(10) Patent No.: US 7,965,917 B2
(45) Date of Patent: Jun. 21, 2011

(54) ILLUMINATING APPARATUS AND SURFACE INSPECTION SYSTEM USING ILLUMINATING APPARATUS

(75) Inventors: Hiroshi Yoshikawa, Kawasaki (JP); Kenji Saitoh, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/764,555

(22) Filed: Jun. 18, 2007

(65) Prior Publication Data
US 2007/0292100 A1    Dec. 20, 2007

(30) Foreign Application Priority Data
Jun. 20, 2006   (JP) .................................. 2006-170042

(51) Int. Cl.
G02B 6/10      (2006.01)
G01N 21/00     (2006.01)
F21S 6/00      (2006.01)
F21V 7/00      (2006.01)

(52) U.S. Cl. ..................... 385/146; 396/267; 356/237.2; 362/257; 362/307; 362/308

(58) Field of Classification Search ................ 396/267; 385/146; 356/237.2–237.5; 362/257, 268, 362/280, 300, 307, 308, 296.1, 311.01, 311.11, 362/311.12
See application file for complete search history.

(56) References Cited

U.S. PATENT DOCUMENTS

| 4,023,903 A * | 5/1977 | Scheib ............................ 355/71 |
| 5,813,743 A | 9/1998 | Naka |
| 6,058,271 A * | 5/2000 | Tenmyo ....................... 396/198 |
| 6,837,595 B2 | 1/2005 | Yoneda |
| 2004/0151008 A1* | 8/2004 | Artsyukhovich et al. ...... 362/572 |
| 2004/0189168 A1* | 9/2004 | Tenmyo ........................ 313/113 |

FOREIGN PATENT DOCUMENTS

| JP | 4-138438 A | 5/1992 |
| JP | 8-262537 A | 10/1996 |
| JP | 2002-310626 A | 10/2002 |
| JP | 2004-301912 A | 10/2004 |
| JP | 2004-354047 A | 12/2004 |
| JP | 8-234277 A | 9/2007 |

* cited by examiner

*Primary Examiner* — Uyen-Chau N Le
*Assistant Examiner* — John M Bedtelyon
(74) *Attorney, Agent, or Firm* — Canon USA Inc. IP Division (57) ABSTRACT

At least one exemplary embodiment is directed to an illuminating apparatus, configured to uniformly illuminate a surface of an object, and includes a light-guiding member configured to guide light emitted from a source to a surface to be illuminated, and a reflecting member disposed between the light-guiding member and the surface to be illuminated. The reflecting member includes a pair of reflection surfaces disposed so as to face each other in a long side direction of the surface to be illuminated, and reflects light emitted from the light-guiding member in directions having directional components parallel to a short side direction of the surface to be illuminated toward the surface to be illuminated.

4 Claims, 10 Drawing Sheets

ILLUMINATING APPARATUS AND SURFACE INSPECTION SYSTEM USING ILLUMINATING APPARATUS

BACKGROUND OF THE INVENTION

1. Field of the Invention

The present invention relates to illuminating apparatuses capable of uniformly illuminating objects to be illuminated or inspected, and relates to surface inspection systems including the illuminating apparatuses.

2. Description of the Related Art

To date, illuminating apparatuses for illuminating an object with light beams emitted from light sources have been used in image pickup apparatuses such as video cameras and digital cameras when the object side is in low light. Such illuminating apparatuses include a light source and optical components such as reflecting mirrors and a Fresnel lens that can efficiently guide light beams emitted from the light source forward (to the object side).

Among such illuminating apparatuses, some illuminating apparatuses can efficiently collect light beams emitted from a light source in many directions into a required illumination field angle.

Moreover, some illuminating apparatuses include optical members using total internal reflection such as a prism light guide instead of a Fresnel lens disposed in front of a light source so as to improve collection efficiency and reduce the size of the apparatuses.

Among these, an illuminating apparatus that illuminates an object with light beams emitted from a light source via a small optical member having a high collection efficiency is well known (see Japanese Patent Laid-Open No. 4-138438).

In the illuminating apparatus discussed in Japanese Patent Laid-Open No. 4-138438, light beams emitted forward from a light source are collected using a lens having a positive refracting power. Moreover, light beams emitted sideward from the light source are guided to a prism, and are reflected forward using total internal reflection. In this manner, light sources emitted in many directions are collected so as to illuminate the object side.

The illuminating apparatus discussed in Japanese Patent Laid-Open No. 4-138438 uses a small high-collectivity optical member capable of collecting light beams emitted from the light source in many directions and emitting the light beams from a common emergent surface.

In particular, the illuminating apparatus discussed in Japanese Patent Laid-Open No. 4-138438 can markedly increase the illuminance in the vicinity of the center of the object.

Moreover, Japanese Patent Laid-Open No. 8-262537 discusses an illuminating apparatus including an illumination optical system reduced in size by disposing a prism with a high collectivity in the anterior position to a light source, and having a light-emergent surface that emits light beams perfectly reflected inside the prism and is inclined with respect to an optical axis.

Moreover, Japanese Patent Laid-Open No. 8-234277 discusses an illuminating apparatus having an optical member using total internal reflection as a light guide located in the vicinity of a light source. The illuminating apparatus collects light beams emitted from the light source and converts the light beams into uniformly distributed light beams using the optical member so as to illuminate a surface with a small optical loss.

In general, illuminating apparatuses used with image pickup apparatuses such as cameras are required to uniformly and efficiently illuminate the object side.

Moreover, illuminating apparatuses used in surface inspection systems for detecting the presence of faults such as scratches, projections, and depressions on inspection surfaces of objects are required to uniformly and brightly illuminate the inspection surfaces of the objects.

In particular, stability in accuracy in detecting faults and durability of the systems are required for the surface inspection systems used for inspecting faults on the inspection surfaces of the objects. In order to improve stability in accuracy in detecting faults, it is useful to maintain sensitivity (accuracy) in detecting faults in the areas of the inspection surfaces of the objects at a constant level. Therefore, uniformity in illumination in the inspection areas is particularly important.

On the other hand, in order to increase the lifetime of, in particular, light-emitting tubes used for light sources, it is useful to efficiently illuminate the inspection surfaces with light beams emitted from the light sources.

In general, illuminance is increased by applying a higher voltage to the light-emitting tubes serving as the light sources, and this leads to a reduction in the lifetime of the light-emitting tubes. Therefore, illuminating apparatuses used in inspection systems for inspecting object surfaces are required to be used with low voltage (low illuminance), and to efficiently illuminate inspection surfaces so as to increase the lifetime of the light-emitting tubes and brightness of illumination.

SUMMARY OF THE INVENTION

At least one exemplary embodiment of the present invention is related to an illuminating apparatus capable of uniformly and efficiently illuminating a surface of an object to be illuminated or inspected, and is related to a surface inspection system including the illuminating apparatus.

An illuminating apparatus according to an exemplary embodiment of the present invention includes a light-guiding member configured to guide light emitted from a light source to a surface to be illuminated, and a reflecting member disposed between the light-guiding member and the surface to be illuminated. The reflecting member includes a pair of reflection surfaces disposed so as to face each other in a long side direction of the surface to be illuminated, and reflects light emitted from the light-guiding member in directions having directional components parallel to a short side direction of the surface to be illuminated toward the surface to be illuminated.

Further features of the present invention will become apparent from the following description of exemplary embodiments with reference to the attached drawings.

DESCRIPTION OF THE EMBODIMENTS

Exemplary embodiments of the present invention will now be described in detail with reference to the drawings.

Figure 1:
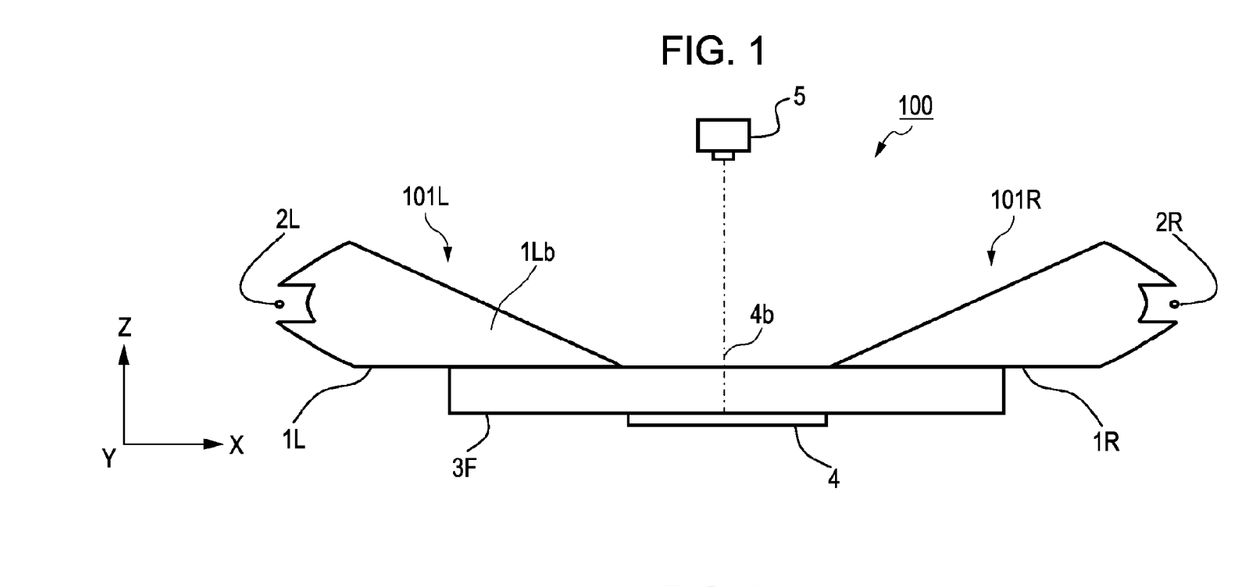
FIG. 1 is a side view of a surface inspection system according to a first exemplary embodiment of the present invention.
Figure 2:
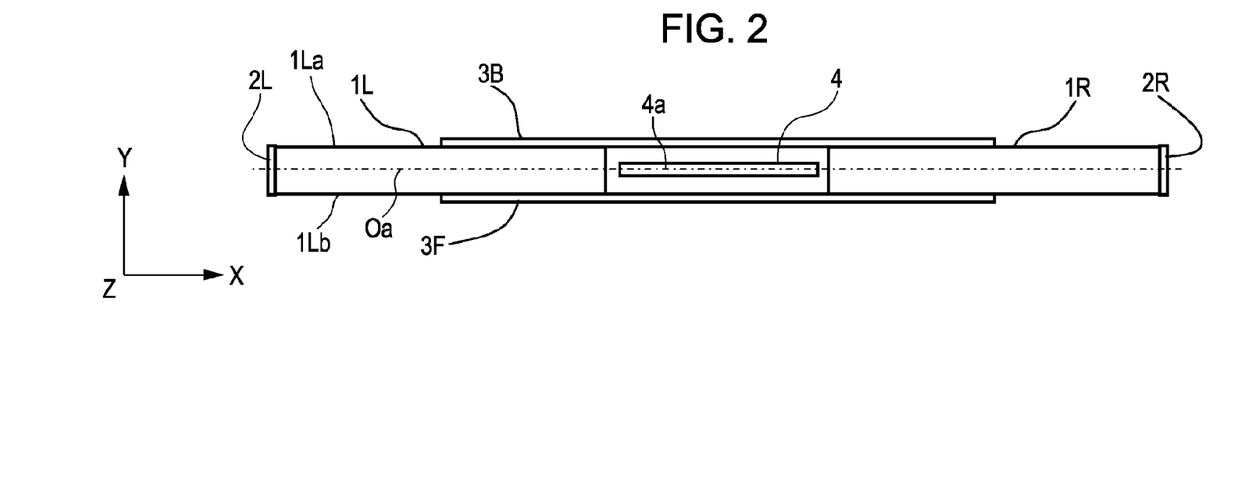
FIG. 2 is a top view of the surface inspection system according to the first exemplary embodiment.
Figure 3:
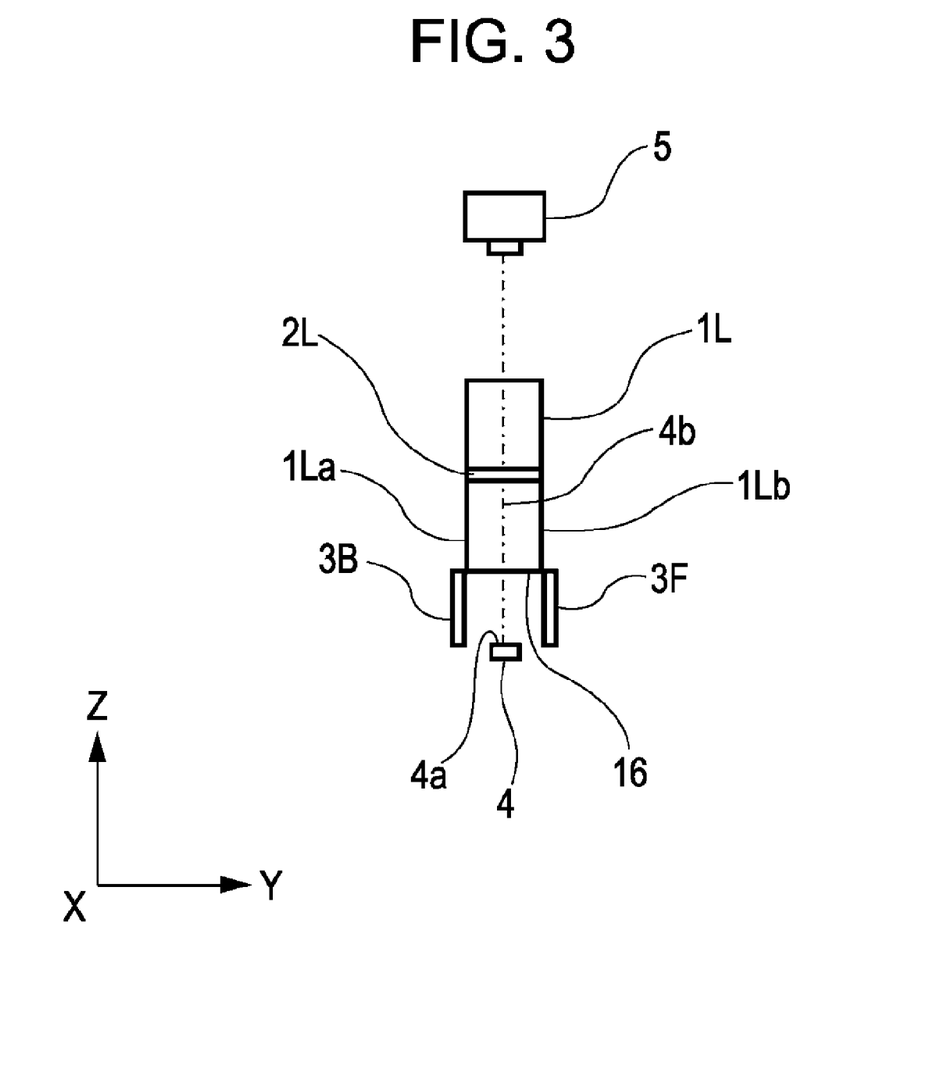
FIG. 3 is a front view of the surface inspection system according to the first exemplary embodiment.

FIGS. 1 to 3 are schematic views of principal parts of a surface inspection system 100 using illuminating apparatuses according to a first exemplary embodiment of the present invention. In the first exemplary embodiment, the surface condition, i.e., the presence of faults such as scratches, projections, and depressions, on an inspection surface (illumination surface) 4a of an object 4 is inspected.

FIGS. 1 to 3 are a side view, a top view, and a front view, respectively, of the surface inspection system and the illuminating apparatuses according to the first exemplary embodiment.

Illuminating apparatuses 101L and 101R (generally referred to as illuminating apparatuses 101) shown in FIGS. 1 to 3 include prisms 1L and 1R (generally referred to as prisms 1), respectively, serving as light-guiding members each having incident surfaces and reflection surfaces.

Light sources 2L and 2R (generally referred to as light sources 2) are disposed so as to face the prisms 1L and 1R, respectively. Mirrors 3F and 3B are disposed so as to face each other along a long side direction of the inspection surface 4a, and have the object 4 interposed therebetween. The mirrors 3F and 3B constitute reflecting members.

The object 4 has a rectangular parallelepiped or a cylindrical shape, and the inspection surface 4a, a part of the object 4, is illuminated with light beams emitted from the illuminating apparatuses 101 (e.g., 101L, 101R). An image pickup apparatus 5 captures images of a part of an illumination area on the object 4 illuminated with light beams emitted from the illuminating apparatuses 101.

The prisms 1L and 1R each constitute a component of a light-guiding member that guides light beams emitted from the light sources 2L and 2R, respectively, to the object 4.

In order to facilitate visualization, the image pickup apparatus 5 shown in FIG. 1 is omitted in FIG. 2. Moreover, the front view shown in FIG. 3 is viewed from the light source 2L shown in FIG. 1.

In this exemplary embodiment, the inspection surface 4a of the object 4 is illuminated with light beams emitted from the illuminating apparatuses 101L and 101R, and images of the inspection surface 4a are captured by the image pickup apparatus 5 such that the surface condition of the inspection surface 4a, for example, the presence of faults, is inspected.

In the first exemplary embodiment, the illuminating apparatus 101L including the prism 1L and the light source 2L is disposed at the left of the object 4, and the illuminating apparatus 101R including the prism 1R and the light source 2R is disposed at the right of the object 4 so as to increase the illuminance and uniformity in illuminance distribution in the illumination area on the object 4.

In this exemplary embodiment, the light sources 2L and 2R can be cylindrical light-emitting tubes. However, the light sources 2L and 2R can be those having spherical light-emitting portions according to the shapes of the prisms 1L and 1R.

Cylindrical light-emitting tubes include, for example, xenon tubes and fluorescent lamps. In particular, xenon tubes for electronic flash devices can be used.

As light sources having spherical light-emergent surfaces, for example, incandescent lamps, light-emitting diodes (LEDs), and halogen lamps can be used.

The image pickup apparatus 5 can be a digital camera, a video camera, and the like having an area sensor such as a charge-coupled device (CCD) and a complementary metal oxide semiconductor (CMOS) sensor or a line sensor.

In the first exemplary embodiment, the image pickup apparatus 5 is disposed above the center of the inspection surface 4a of the object 4 in the vertical direction.

Since no refracting members such as prisms are disposed between the image pickup apparatus 5 and the inspection surface 4a, excellent images without aberration caused by refracting members can be captured.

The inspection surface 4a is illuminated with light beams emitted from the illuminating apparatuses 101L and 101R in a direction oblique to a normal line 4b of the inspection surface 4a. Since the illuminating beams are inclined with respect to the inspection surface 4a, the image pickup apparatus 5 observes the object 4 using diffuse reflected light beams reflected from the inspection surface 4a. Therefore, the image pickup apparatus 5 captures dark-field images.

However, images captured by the surface inspection system 100 according to this exemplary embodiment are not limited to dark-field images. When the image pickup apparatus 5 is disposed at an angle symmetrical to the incident angle of the illuminating beams, bright-field images formed using specular reflected light beams reflected from the inspection surface 4a can be captured by the image pickup apparatus 5.

Figure 4A:
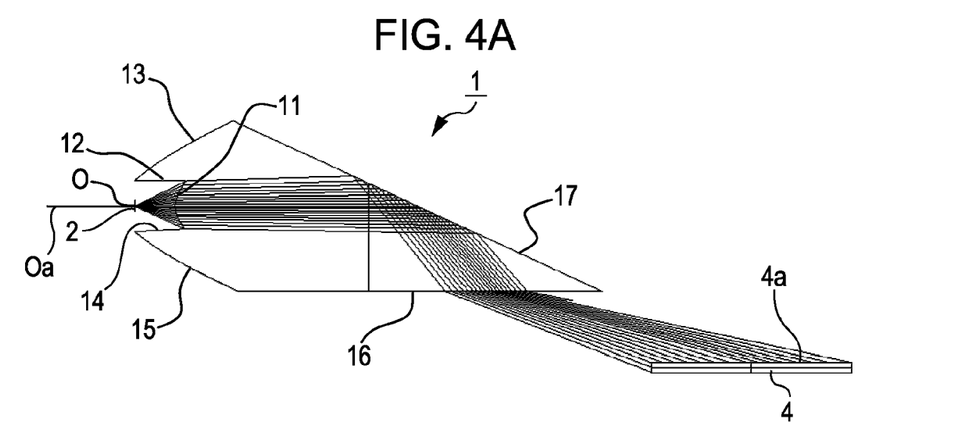
FIGS. 4A to 4C are enlarged views of a part in the vicinity of a side surface of a prism shown in FIG. 1, illustrating light beams traced from a light source.
Figure 4B:
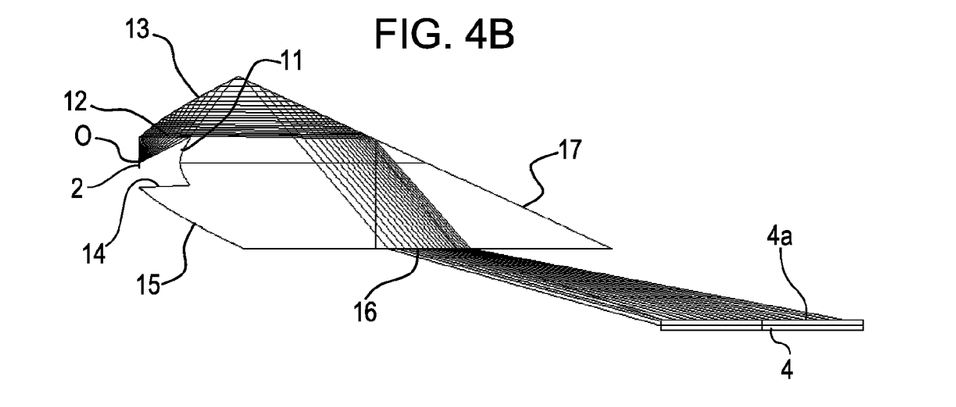
Figure 4C:
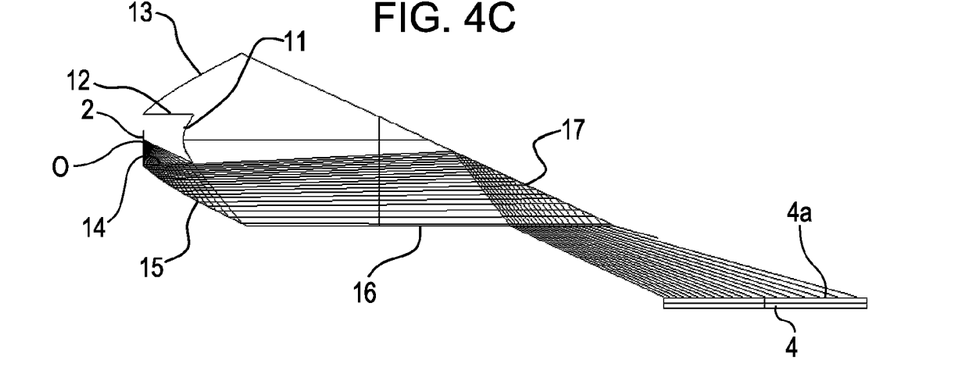

FIGS. 4A to 4C are enlarged views of a side surface of one of the prisms 1 and the object 4, and illustrate light beams traced from one of the light sources 2.

The prism 1 includes a first incident surface 11, a second incident surface 12, a third incident surface 14, a first reflection surface 17, a second reflection surface 13, a third reflection surface 15, and an emergent surface 16.

The first incident surface 11 can be curved, and has a light-collecting function. The reflection surfaces 13, 15, and 17 that reflect incident beams can be formed by applying metallic films.

Figure 5:
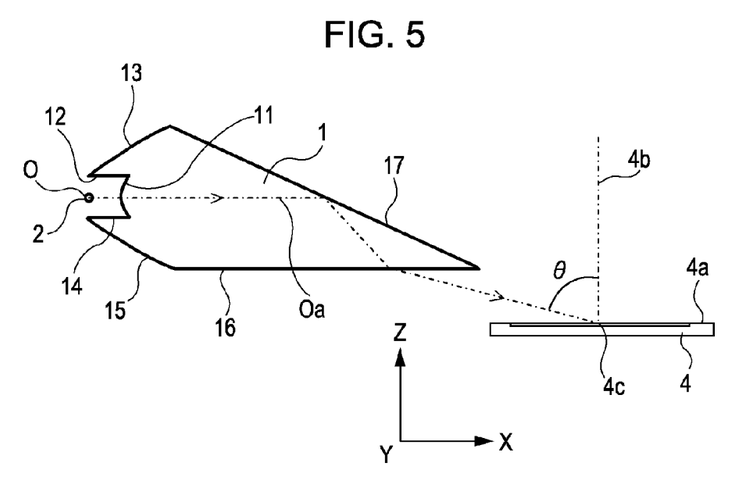
FIG. 5 is an enlarged view of the part in the vicinity of the side surface of the prism shown in FIG. 1, illustrating light beams traced from the light source.

FIG. 5 illustrates a light beam located on an optical axis 4b along which the light beams are emitted among light beams emitted from the light source 2. The light beam is incident on the first incident surface 11 of the prism 1, and is perfectly reflected from the first reflection surface 17. Subsequently, the light beam is emitted from the emergent surface 16, and then enters an incident point 4c on the inspection surface 4a at an incident angle θ.

Herein, the optical axis 4b is a line connecting a light-emitting point (light-emitting center) O of the light source 2 and the center of curvature of the first incident surface 11. The light-emitting center of the light source corresponds to the central axis of a cylinder when the light source is formed of a cylindrical light-emitting tube, and corresponds to the center of a sphere when the light source is formed of a spherical light-emitting portion.

In this exemplary embodiment, a plane (X-Z plane) including the optical axis 4b and the normal line 4b at the incident point 4c on which the light beam located on the optical axis 4b is incident is referred to as a reference plane.

As shown in FIG. 4A, light beams located on and in the vicinity of the optical axis 4b among those emitted from the light-emitting point O of the light source 2 are incident on the first incident surface 11. The light beams are reflected from the first reflection surface 17, and emitted from the emergent surface 16.

On the other hand, as shown in FIG. 4B, light beams emitted upward away from the optical axis 4b with a large angle among those emitted from the light-emitting point O are incident on the second incident surface 12. The light beams are perfectly reflected from the second reflection surface 13, reflected from the first reflection surface 17, and then emitted from the emergent surface 16.

Moreover, as shown in FIG. 4C, light beams emitted downward away from the optical axis 4b with a large angle among those emitted from the light-emitting point O are incident on the third incident surface 14. The light beams are perfectly reflected from the third reflection surface 15, reflected from the first reflection surface 17, and then emitted from the emergent surface 16.

All the light beams emitted from the light-emitting point O are deflected from the first reflection surface 17 using total internal reflection, and emitted from the emergent surface 16 such that the inspection surface 4a of the object 4 are illuminated in a direction oblique to the object 4.

In this manner, the inspection surface 4a is efficiently illuminated by refraction and total internal reflection of light beams emitted forward (to the side of the object 4) from the light sources 2 using the prisms 1L and 1R having the above-described shape.

Some light beams among those incident on the first incident surface 11 are directly emitted from the emergent surface 16 without being reflected.

Moreover, some light beams among those reflected from the second reflection surface 13 or the third reflection surface 15 are directly emitted from the emergent surface 16.

Figure 6:
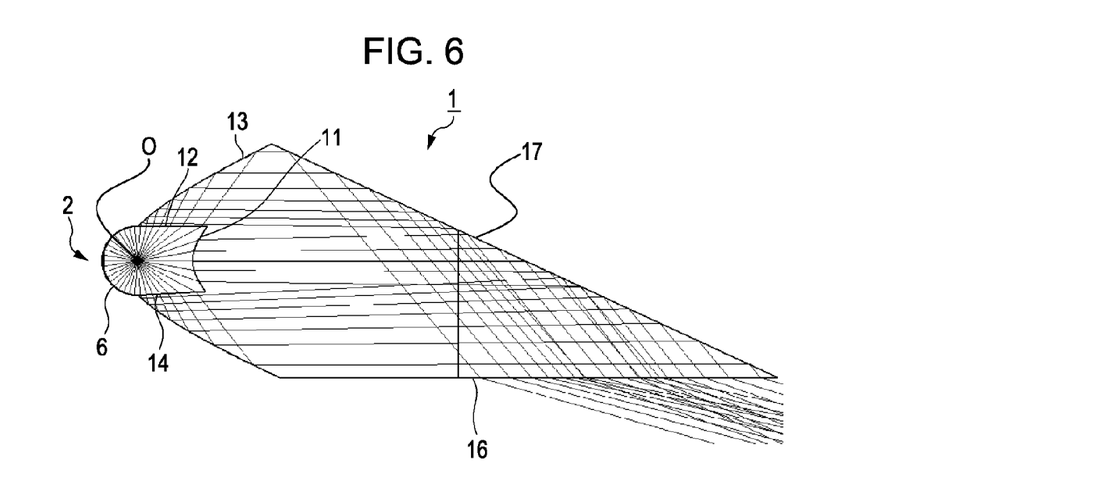
FIG. 6 is a side view when a cylindrical mirror is disposed behind the light source, illustrating light beams traced from the light source.

As shown in FIG. 6, light beams emitted backward (to the side opposite to the side of the object 4) from the light source 2 can be reflected using a cylindrical mirror 6 disposed such that the light-emitting point O of the light source 2 is located on the central axis of the cylindrical mirror 6. With this arrangement, the inspection surface 4a can be efficiently illuminated.

The light beams emitted backward from the light-emitting point O of the light source 2 are reflected from the cylindrical mirror 6 so as to be returned to the light-emitting point O, and then emitted at angles different from the original emission angles by 180°, i.e., in opposite directions. The light beams emitted in the opposite directions travel on the same paths as light beams emitted forward, and are incident on the inspection surface 4a.

Since the absorption at the reflection surface of the cylindrical mirror 6 is the only cause of the optical loss of the light beams emitted backward, efficient illumination can be realized.

The incident angle θ of the light beam on the optical axis 4b emitted from the emergent surface 16 of the prism 1 to the object 4 can be set to 75°±10° (65°<θ<85°). This is useful because a large incident angle can increase the detectivity of faults (scratches, dust, or the like) on an object surface when dark-field images are used for observation.

As shown in FIGS. 1 to 3, the mirrors 3F and 3B are disposed between the emergent surfaces 16 of the prisms 1 and the object 4. The mirrors 3F and 3B are disposed parallel to the reference plane (X-Z plane) in the long side direction of the inspection surface 4a so as to face each other, and have the optical axis 4b interposed therebetween.

Moreover, as shown in FIG. 2, the mirrors 3F and 3B are disposed on planes extending from side surfaces 1La and 1Lb of the prism 1L (planes parallel to the X-Z plane) so as to be parallel to each other.

With this structure, light beams emitted from the emergent surfaces 16 of the prisms 1 and directed to the side surfaces of the prisms 1 (in the Y direction), i.e., light beams having directional components parallel to the short side direction of the inspection surface 4a (perpendicular to the reference plane; X-Z plane), are reflected toward the inspection surface 4a.

The number of light beams incident on the inspection surface 4a of the object 4 can be increased by reflecting the light beams emitted from the emergent surfaces 16 using the mirrors 3F and 3G. This leads to an efficient illumination and an improvement in uniformity in illuminance distribution on the surface of the object 4 in both the long side and short side directions.

Next, the reasons the number of light beams incident on the object 4 are increased and uniformity in illuminance distribution on the object 4 in the long side direction (X direction) is increased by using the mirrors 3F and 3B will be described with reference to FIGS. 7A and 7B.

Figure 7A:
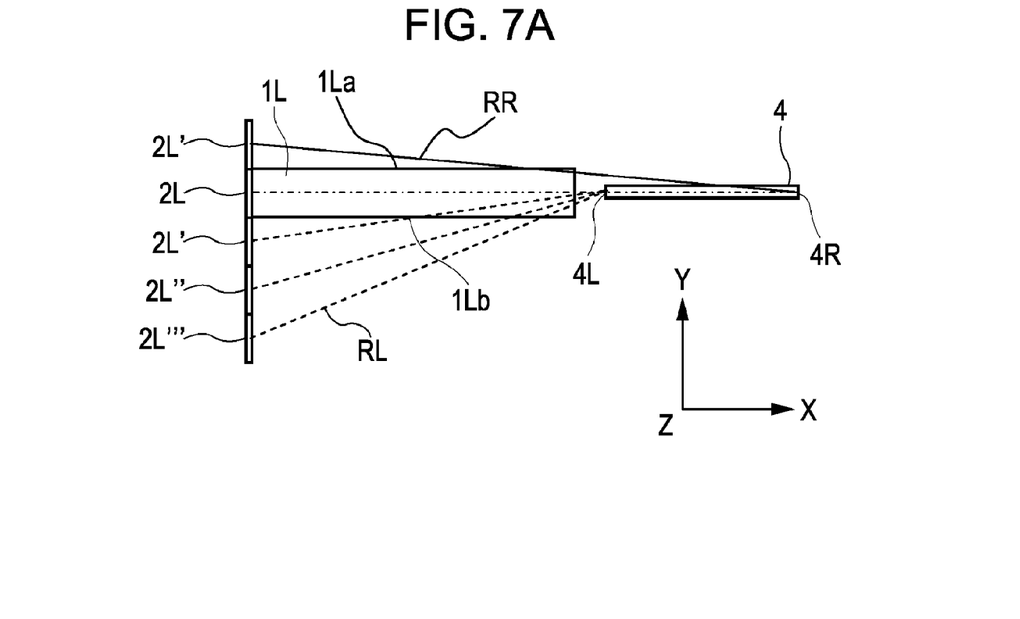
FIGS. 7A and 7B are top views illustrating how illuminance on an illumination surface of an object is increased.
Figure 7B:
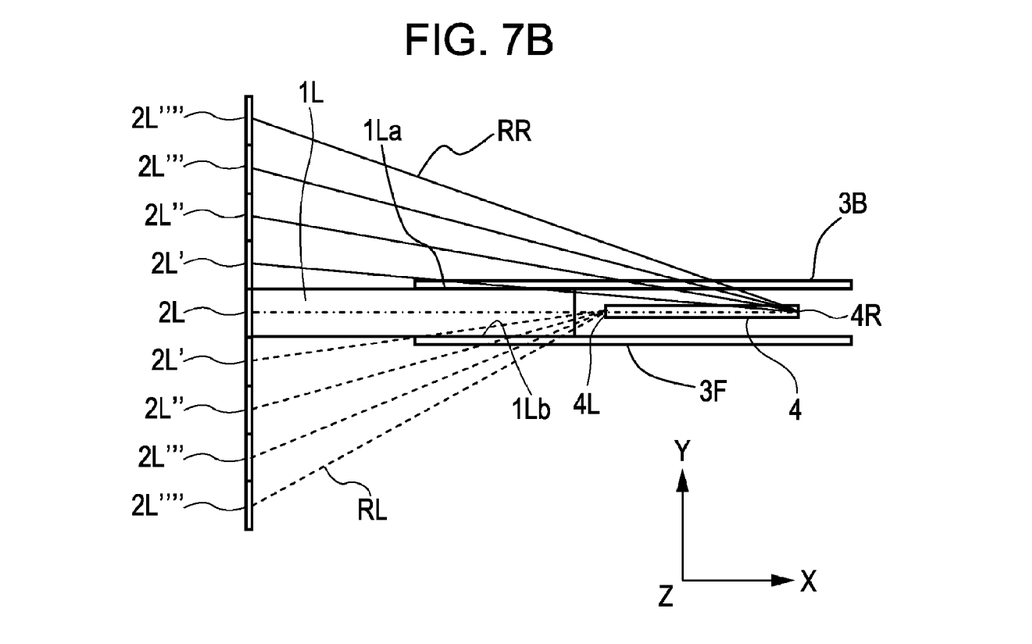

FIG. 7A is a top view when the mirrors 3F and 3B are not used, and FIG. 7B is a top view when the mirrors 3F and 3B are used.

In order to simplify explanation, only one (at the left) of the prisms 1 is illustrated. Moreover, the image pickup apparatus 5 is omitted.

Light beams emitted from the light source 2L are reflected from the side surfaces 1La and 1Lb of the prism 1 in accordance with emission directions thereof, and are incident on the inspection surface 4a of the object 4. When viewed from the illumination surface of the object 4, this phenomenon can be considered as being due to light beams being emitted from a plurality of virtual light sources.

That is, light beams reflected from the side surfaces 1La and 1Lb of the prism 1L one time correspond to those emitted from a secondary light source 2L' of the light source 2L. Light beams reflected from the side surfaces 1La and 1Lb of the prism 1L two times corresponds to those emitted from a tertiary light source 2L" of the light source 2L.

In FIGS. 7A and 7B, light beams emitted from the virtual light sources 2L', 2L", . . . of the light source 2L are illustrated, whereas those reflected from the side surfaces 1La and 1Lb are not illustrated.

In FIGS. 7A and 7B, light beams RL emitted from the light sources 2L, 2L', 2L", . . . are incident on the left end 4L of the object 4, and light beams RR emitted from the light sources 2L, 2L', 2L", . . . are incident on the right end 4R of the object 4. When no mirrors are used as shown in FIG. 7A, light beams incident on the left end 4L of the object 4 are perfectly reflected from the side surfaces 1La and 1Lb of the prism three times.

Thus, light beams emitted from a quaternary light source 2L''' are incident on the left end 4L of the object 4. On the other hand, light beams incident on the right end 4R of the object 4 are perfectly reflected from the side surfaces 1La and 1Lb of the prism only one time.

Therefore, only the light beams emitted from the light source 2L' are incident on the right end 4R, and other light beams emitted from the prism 1 are scattered in the Y direction.

Accordingly, the ratio of the number of light sources viewed from the left end 4L to the number of light sources viewed from the right end 4R of the object 4 becomes 7:3, resulting in poor uniformity in illuminance distribution in the long side direction of the object 4 (X direction).

On the other hand, when the mirrors 3F and 3B are used as shown in FIG. 7B, light beams emitted from up to a quinary light source 2L"" are incident on both the left end 4L and the right end 4R of the object 4.

Therefore, the ratio of the number of light sources at the left end 4L to the number of light sources at the right end 4R becomes 9:9, and uniformity in illuminance distribution in the long side direction of the object 4 (X direction) can be improved as compared with the case of the ratio of 7:3 when the mirrors 3F and 3B are not used. Moreover, the illuminance is also increased since the entire number of light sources is increased.

Figure 8:
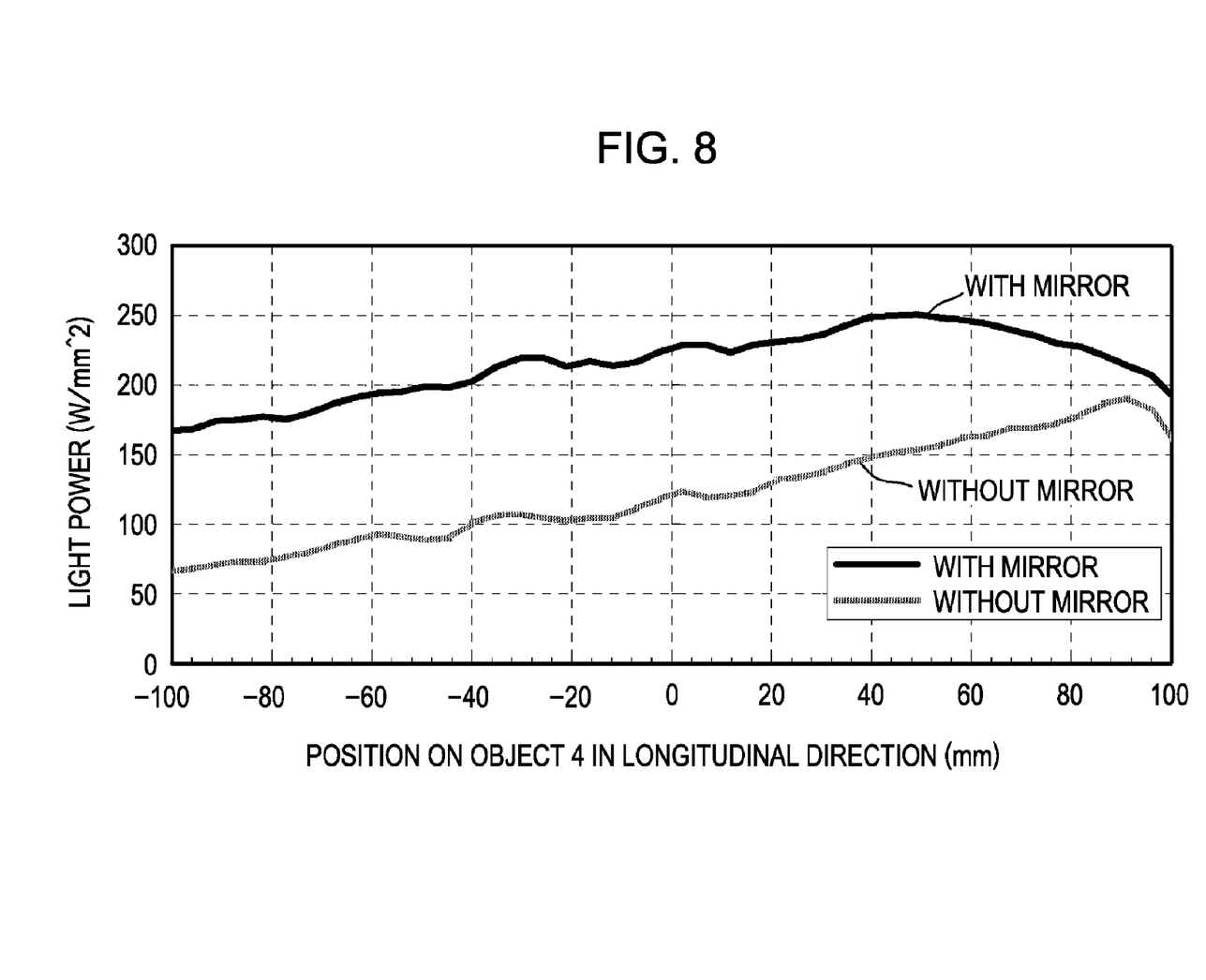
FIG. 8 illustrates illuminance distributions in a long side (longitudinal) direction of a surface of an object obtained using illumination simulation.

Illumination analysis was carried out using a software program capable of non-sequential ray-tracing and light intensity simulation. FIG. 8 illustrates illuminance distributions in the long side direction of the object 4 when the mirrors 3F and 3B were used and when no mirrors were used. The simulation was carried out for a case of illumination from only one side.

As shown in FIG. 8, the illuminance when the mirrors were used was higher than that when no mirrors were used over the entire illumination range in the long side direction. When the mean values of the illuminances were compared, the illuminance, when the mirrors were used, was approximately 1.75 times higher than that when no mirrors were used.

Moreover, uniformity in illuminance distributions was evaluated using an expression of ((maximum value−minimum value)/mean value). The uniformity when the mirrors 3F and 3B were used was 0.44 whereas the uniformity when no mirrors were used was 1.06. That is, fluctuations in the illuminance with respect to the mean value were reduced by approximately 0.42 times by using the mirrors, resulting in an improvement in uniformity in illuminance distribution.

With consideration of the simulation results, experiments were carried out for verification. According to the experimental results, the mean value of the illuminance when the mirrors 3F and 3B were used was approximately 1.4 times larger than that when no mirrors were used. Moreover, when uniformity in illuminance distributions was evaluated using the expression of ((maximum value−minimum value)/mean value), fluctuations in the illuminance when the mirrors 3F and 3B were used were reduced by 0.56 times as compared with those when no mirrors were used, resulting in an improvement in uniformity in illuminance distribution.

As described above, it was shown by the simulation results and the experimental results that the absolute value of the illuminance could be increased and uniformity in illuminance distribution in the long side direction of the object 4 can be improved when the mirrors 3F and 3B were used.

Figure 9:
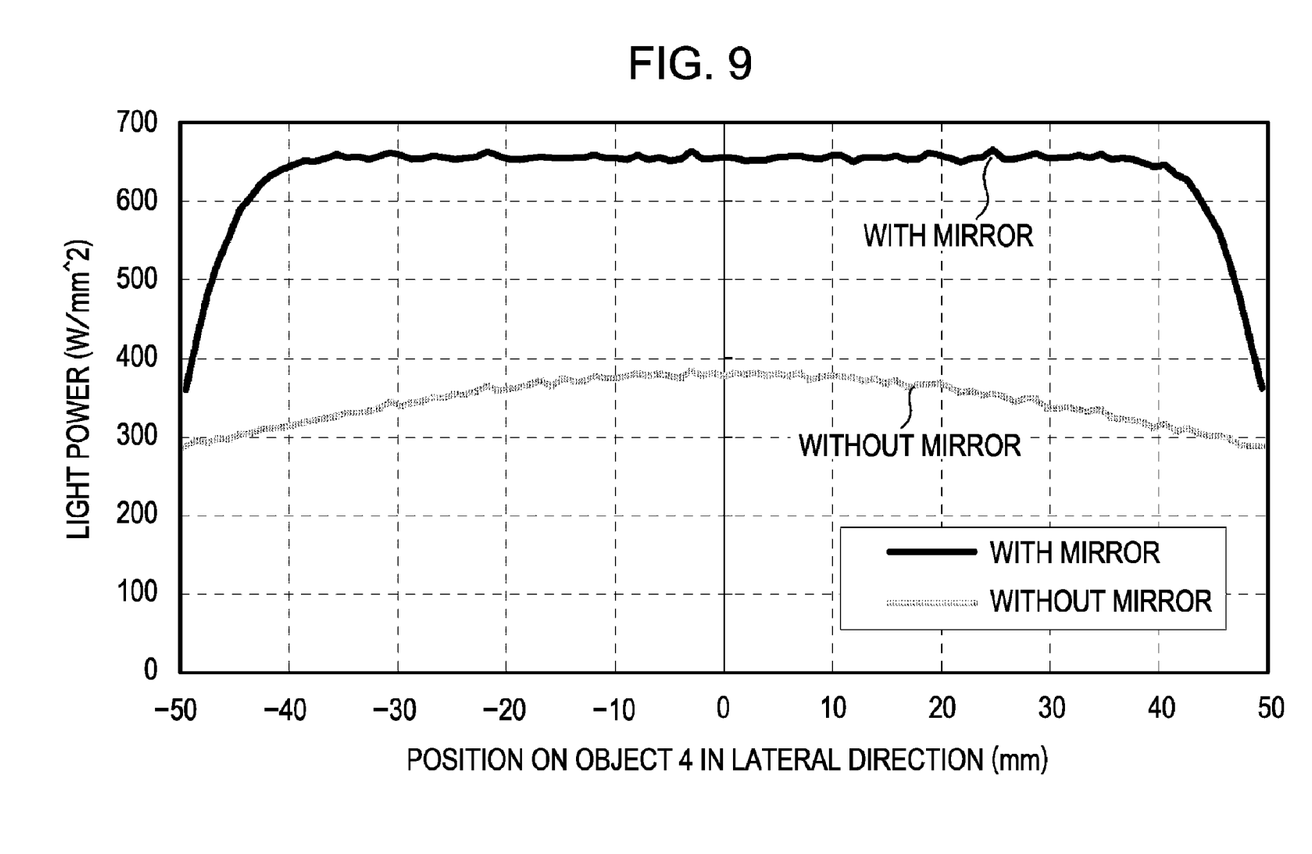
FIG. 9 illustrates illuminance distributions in a short side direction of the surface of the object obtained using the illumination simulation.

Next, the reason uniformity in illuminance distribution on the object 4 in the short side direction (Y direction) is increased will be described. When the mirrors 3F and 3B are not used, light beams emitted from the prism 1 and heading to directions other than the Y direction mainly reach the vicinity of the center of the inspection surface 4a in the short side direction thereof.

Therefore, when the mirrors 3F and 3B are not used, the number of light beams incident on the vicinity of the center of the inspection surface 4a in the short side direction is large, whereas the number of light beams incident on end portions of the inspection surface 4a remote from the center of the inspection surface 4a is small.

Accordingly, illuminance is high at the central portion, and low at the end portions in the short side direction, resulting in poor uniformity in illuminance distribution in the short side direction.

When the mirrors 3F and 3B are used, light beams reflected from the mirrors 3F and 3B and incident on the inspection surface 4a mainly enter the end portions of the inspection surface 4a in the short side direction thereof. Therefore, differences in the number of light beams at the central portion and at the end portions of the inspection surface 4a in the short side direction can be reduced, and thus uniformity in illuminance distribution in the short side direction can be improved.

Illumination analysis in the short side direction (Y direction) of the object 4 was carried out using the same software program used for the analysis in the long side direction (X direction) of the object 4.

FIG. 9 illustrates illuminance distributions in the short side direction of the object 4 when the mirrors 3F and 3B were used and when no mirrors were used. The values of illuminances are mean values of those in the long side direction.

When no mirrors were used, the illuminance in the central portion was high as compared with those in the peripheral portions as shown in FIG. 9 since light beams mainly enter the vicinity of the center of the object 4 in the short side direction.

On the other hand, the profile of the illuminance distribution when the mirrors 3F and 3B were used had a wide flat area although the illuminance steeply declined at the end portions of the profile. Moreover, the absolute value of the illuminance was approximately doubled.

It is useful if surface inspection systems have high uniformity in illuminance distribution, and the mirrors 3F and 3B can increase the inspection range on the inspection surface 4a in the short side direction.

That is, when no mirrors are used, it is useful to dispose an object to be inspected in the vicinity of the center where the illuminance distribution is relatively uniform.

Figure 10:
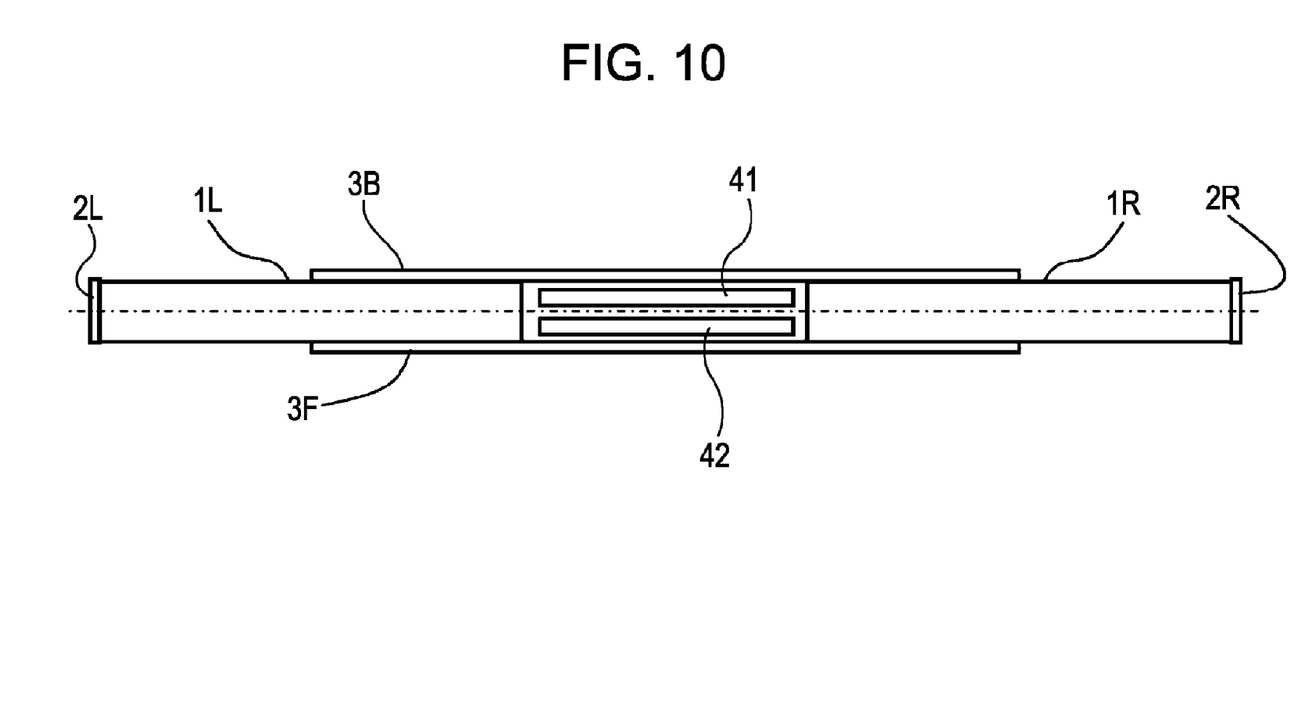
FIG. 10 is a top view of the surface inspection system on which two objects to be inspected are disposed in parallel.

In contrast, when the mirrors 3F and 3B are used, a large number of objects can be disposed in parallel in the short side direction, and can be inspected at the same time.

FIG. 10 is a top view when two objects 41 and 42 are disposed in parallel in the short side direction. With this arrangement, more objects can be inspected during the same period of time. Accordingly, surface inspection systems capable of fast inspection as compared with those according to the known technologies can be built.

Moreover, when a light-emitting tube for an electronic flash device is used as a light source, the lifetime of the light-emitting tube can be increased since the number of light emission per one object can be reduced.

Figure 11A:
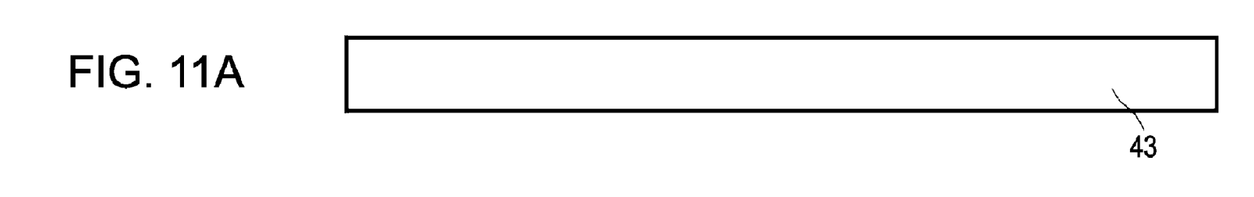
FIGS. 11A to 11C illustrate mirrors applicable to the mirrors in the first exemplary embodiment.
Figure 11B:
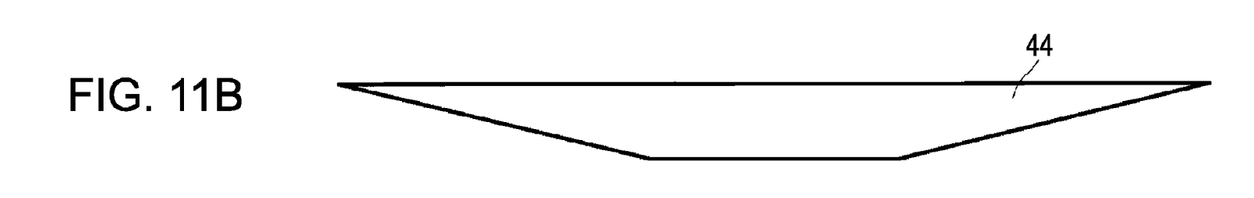
Figure 11C:
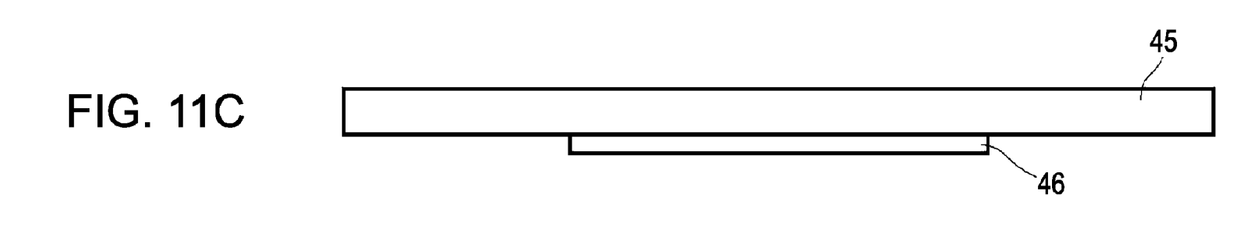

In the first exemplary embodiment, a rectangular mirror 43 shown in FIG. 11A is used as the mirrors 3F and 3B. However, a trapezoidal mirror 44 shown in FIG. 11B, which has the minimum shape along the light paths, can be used when light paths are known.

This leads to space-saving mirrors, and eases restrictions on designing of driving systems during building of surface inspection systems. Moreover, two rectangular mirrors 45 and 46 arranged as shown in FIG. 11C can also be used.

When one wants to illuminate the object 4 with light beams having a specific illuminance distribution, the illuminance distribution can be controlled by changing the shapes and the lengths of the mirrors. For example, when an illuminance distribution in which the illuminance is high at the central portion in the short side direction is required, the width of the mirrors can be reduced as compared with the distance between the prisms and the inspection surface 4a.

Figure 12:
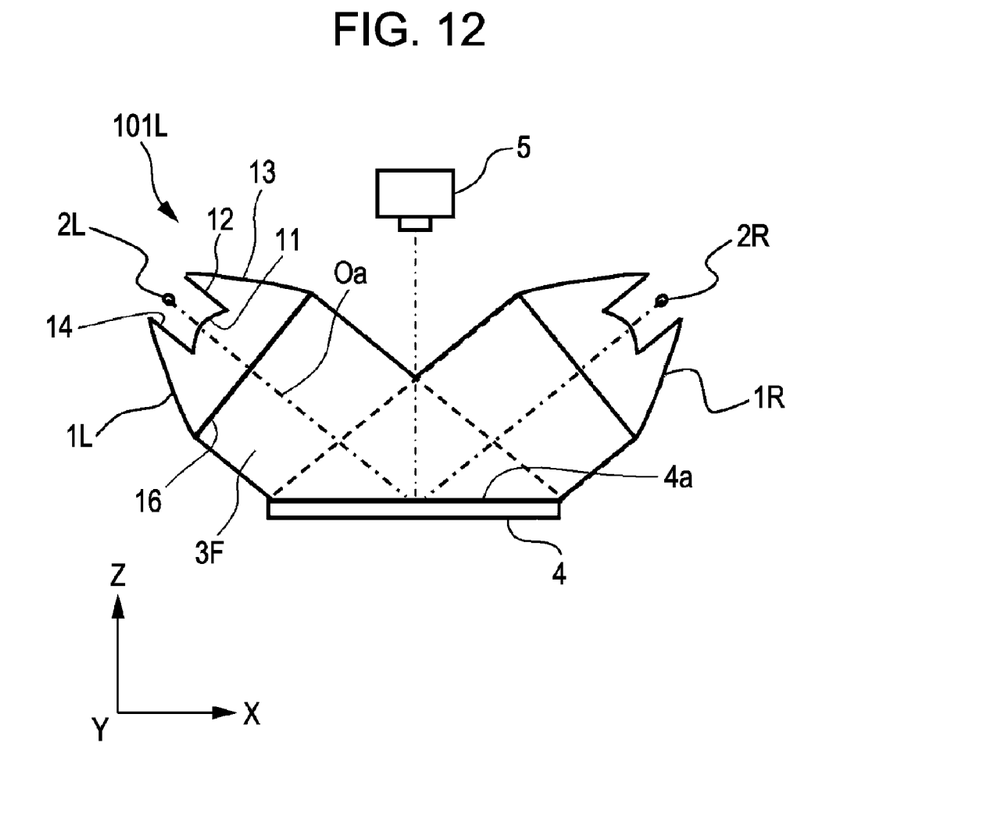
FIG. 12 is a side view of an illuminating apparatus according to a second exemplary embodiment of the present invention.

FIG. 12 is a side view of an illuminating apparatus according to a second exemplary embodiment of the present invention. Unlike the prisms shown in the first exemplary embodiment, prisms 1L and 1R according to the second exemplary embodiment are of a type used in, for example, general illumination systems in electronic flash devices installed in cameras for photography.

In FIG. 12, the shape of a mirror 3F serving as a reflecting member disposed between the prisms 1L and 1R and an object 4 is optimized to a minimum range for covering light paths. The mirror 3F has a complicated shaped due to the optimization. However, the same effect can also be produced when a mirror having a simple trapezoidal reflection surface including the minimum range is used.

Only the mirror 3F is shown in FIG. 12. However, another mirror (reflecting member) 3B is disposed at a position remote from the mirror 3F in a direction perpendicular to the direction of the side view shown in FIG. 12.

In FIG. 12, the prism 1L includes a first incident surface 11, a second incident surface 12, and a third incident surface 14 on which light beams emitted from a light source 2L are incident, and an emergent surface 16 from which the light beams passing through the incident surfaces are emitted toward the object 4.

The reflecting members 3F and 3B (not shown) are disposed between the emergent surface 16 of the prism 1L and the object 4, and are parallel to the reference plane (X-Z plane) so as to face each other having the optical axis 4b interposed therebetween.

With this structure, the mirror 3F and 3R reflect light beams emitted from the emergent surface 16 and having directional components perpendicular to the reference plane (X-Z plane) toward the inspection surface 4a.

According to the above-described exemplary embodiments, illuminating apparatuses capable of efficiently collecting light beams emitted from light sources in many directions into a required illumination field angle and surface inspection systems including the same can be realized.

While the present invention has been described with reference to exemplary embodiments, it is to be understood that the invention is not limited to the disclosed exemplary embodiments.

This application claims the priority of Japanese Application No. 2006-170042 filed Jun. 20, 2006, which is hereby incorporated by reference herein in its entirety.

What is claimed is:

1. An illuminating apparatus for illuminating a surface to be illuminated, the illuminating apparatus comprising:

a light-guiding member configured to guide light emitted from a light source to the surface to be illuminated, a prism member included in the light-guiding member; and a reflecting member disposed between the light-guiding member and the surface to be illuminated, wherein the reflecting member includes a pair of reflection surfaces disposed so as to face each other along a predetermined direction, wherein the reflection surfaces reflect light emitted from the light-guiding member in directions having directional components perpendicular to the predetermined direction toward the surface to be illuminated, wherein the pair of reflection surfaces are planes and are disposed parallel to each other and so as to have the surface to be illuminated interposed therebetween, wherein a length of each reflection surface along the predetermined direction is greater than a distance between the reflection surfaces, wherein the pair of reflection surfaces reflects at least a majority of the light emitted onto the pair of reflection surfaces by the light-guiding member, and wherein the prism member includes a first incident surface, a second incident surface, and a third incident surface on each of which a part of light emitted from the light source is incident; a first reflection surface from which the light incident on the first incident surface is reflected, a second reflection surface from which the light incident on the second incident surface is reflected to the first reflection surface, and a third reflection surface from which the light incident on the third incident surface is reflected to the first reflection surface; and an emergent surface from which the light reflected from the first reflection surface is emitted.

2. A surface inspection system comprising:

an illuminating apparatus according to claim 1 configured to illuminate a surface to be inspected on an object; and an image pickup apparatus configured to capture images of the illuminated surface to be inspected.

3. The surface inspection system according to claim 2, wherein an angle θ formed between an exit optical axis of the illuminating apparatus and an optical axis of the image pickup apparatus satisfies the following condition:

$65° < θ < 85°$.

4. The surface inspection system according to claim 2, wherein the image pickup apparatus captures images of the surface to be inspected without using a refracting member.

* * * * *